United States Patent [19]

Dickie et al.

[11] Patent Number: 5,055,045
[45] Date of Patent: Oct. 8, 1991

[54] DISPOSABLE DENTAL MATRIX RETAINER CLAMP

[76] Inventors: Robert G. Dickie, 15 Valley Trail, R.R. #1, Newmarket, Ontario L3Y 4V8; Volker W. Stein, 235 Eagle Street, Newmarket, Ontario L3Y 1J8, both of Canada

[21] Appl. No.: 670,621
[22] Filed: Mar. 18, 1991
[51] Int. Cl.$^5$ .............................................. A61C 5/04
[52] U.S. Cl. ..................................... 433/155; 433/39
[58] Field of Search .................... 433/39, 40, 155, 156, 433/157

[56] References Cited

U.S. PATENT DOCUMENTS

| | | | |
|---|---|---|---|
| 2,502,903 | 4/1950 | Toffelmire | 433/155 |
| 2,686,970 | 8/1954 | Reiter | 433/155 |
| 3,516,162 | 6/1970 | Ainsworth | 433/155 |
| 4,915,627 | 4/1990 | Hirdes | 433/155 |

OTHER PUBLICATIONS

"Ultrix ® Bulk Matrix Kits and Bands", Advertisement of Hoechst AG, West Germany, Undated.

Primary Examiner—Cary E. O'Connor

[57] ABSTRACT

A dental matrix retainer package includes a plastic matrix retainer clamp which permits a matrix band to be unlocked from its tightened position over a tooth without releasing the matrix band from the clamp entirely, permits a matrix band to be swiveled to accommodate different mouth quadrants with removal for reorientation, permits rapid retraction of a matrix band from a tooth, and permits careful tightening of a matrix band over a tooth in order to avoid the possibility of overtightening. The package is designed so that it must be entirely disposed of after use on a patient, thereby providing maximum assurance against cross contamination.

21 Claims, 3 Drawing Sheets

DISPOSABLE DENTAL MATRIX RETAINER CLAMP

TECHNICAL FIELD

This invention relates generally to tools for use by the dental profession and more particularly to dental matrix clamps, which are used to position matrix retainer bands for temporarily replacing missing portions of teeth following cavity preparation so that amalgams, composite resins, or temporary dressings may be inserted.

BACKGROUND OF THE INVENTION

When working on posterior teeth, a dentist generally uses a metal matrix retainer band which measures approximately a thousandth of an inch in thickness and is approximately eight millimeters wide. In order to place the band around a tooth, a holding mechanism is required. This mechanism is commonly known as a matrix retainer clamp and typically consists of an end into which the ends of the looped matrix band are inserted and tightened into place, as well as a shaft through which a sliding tightening screw allows for adjustment of the matrix band. At the same time, the shaft provides the dentist with a way of holding the matrix band for placement.

Once in place around the tooth and tightened, the band, due to curvature or angulation of the head of the retainer clamp, pulls tightly around the gingival margin (area of the cavity prep that approximates the gum tissue). Due to the anatomical shape of many teeth the interproximal wall becomes concave, thereby leaving an opening through which filling material would push upon condensation. Placement of a wooden triangular wedge between the adjacent tooth and the matrix band is required not only to tighten the band to the tooth but also to spread the teeth slightly apart so that upon matrix band removal the teeth will still make contact proximally.

In North America, the most common matrix retainer clamp is the Toffelmire Matrix Retainer. The retainer clamp is made of stainless steel, with three choices in the head for placement of the band: (1) left side upper or right side lower, (2) right side upper or left side lower, or (3) straight. The shaft contains a long tightening screw with exposed threads. Thoughtful care must be exercised to avoid binding the lip tissue into the screw during the tightening procedure. Furthermore, due to the exposure of the thread mechanism, continuous lubrication is required to keep the action moving freely.

During the wedging procedure, it is common to access the proximal area from the palatal or lingual (tongue) side. In situations where a tooth has an anomalous shape or position, however, it is sometimes necessary to wedge from the vestibular (cheek) side. This is not always possible with the Toffelmire Matrix as the retainer head usually blocks the desired passage to the interproximal area.

Although it is possible to cut the matrix band for removal from the tooth by pulling the band laterally, in practical terms the band is loosened and slipped off the tooth in the reverse of the placement procedure and following wedge removal. Since the Toffelmire Matrix Retainer has only one vertical stop the band can twist out of the head and become difficult to remove without damaging the filling.

Most dental offices work with a tray set up for each type of procedure. It would be necessary to have at least two Toffelmire Matrix Retainers on each filling tray to allow for location choice and sterilization. In practical terms, it is apparent that clinicians often have only two retainers per operatory and use a cold sterilization technique, usually with a new band for each patient. With the advent of highly infective diseases such as Hepatitis B and AIDS, along with the placement of the matrix band in an area that bleeds readily, it would be prudent to have a band retainer mechanism which eliminates any possibility of cross contamination, i.e., one which is disposable as a single entity.

SUMMARY OF THE INVENTION

From one aspect, the present invention is a disposable dental matrix retainer clamp designed so that it, along with the matrix retainer band used, must be discarded after use upon a patient. In other words, from this aspect of the invention, a retainer band once installed in the clamp cannot be disposed of separately, requiring the band and the clamp to be discarded together. From another aspect, the invention is a complete system comprising not only the matrix retainer clamp itself but also the required metal matrix band. From this aspect, the invention can be described as an "Omni-Matrix System" and represents a complete tool that is purchased by a dentist as an entity and is disposed of as an entity after use upon a patient. From yet another aspect, the invention permits a matrix band to be used in any of the possible mouth quadrants without special assembly within the clamp. From still another aspect, the invention permits both rapid retraction of a band from a tooth and fine control in tightening the band in order to avoid the possibility of overtightening. From a further aspect, a dental matrix clamp in accordance with the invention is fabricated with its principal parts all or mostly of plastic, thus further emphasizing ready disposability.

As a disposable matrix retainer clamp for use with a matrix band having a hole at each end and which, when formed, comprises a central loop and flat aligned end sections each containing one of the holes, the invention includes a hollow shaft in the form of a tube with threads extending longitudinally along at least a portion of its interior. Within the tube, a block extends longitudinally and has its own threaded shaft extending from one end and mating with the threads of the tube. A head element is provided at the end of the tube containing the end of the block opposite the shaft. The head element contains a slot for receiving the flat end section of a matrix band with its holes extending beyond the head element into the interior of the tube. A pin is spring mounted on the end of the block nearest the head element for engaging the holes of a matrix band having its end sections extending through the head element slot. At least one wedge with its narrow end extending in the direction toward the block is mounted longitudinally within the tube to engage the mounting of the pin and lift the pin clear of the holes of a matrix band having its end sections extending through the head element slot when the matrix band is moved into its extreme extended position with respect to the block. Finally, an adjusting knob is attached to the threaded shaft of the block at the end of the tube opposite to the head element. In such a retainer clamp, the block moves in one direction under the control of the knob to tighten the loop of a matrix band mounted with its end sections extending through the head element slot and in the opposite direction to cause the wedge to release the pin from the matrix band holes, thereby permitting the band to be removed from a tooth. Once the pin has been released from the matrix band holes, the matrix band cannot be reinstalled. Thus, the clamp and the band must be discarded after use as a single entity.

As a complete tool, the invention takes the form of the matrix retainer clamp just described plus a matrix band having a hole at each end and comprising, when formed, a central loop and flat aligned end sections each containing one of the holes and mounted with its end sections extending through the head element slot. The matrix band is pre-installed in the clamp in its fully extended position with respect to the head element, permitting it to be slipped over a tooth, tightened when required, and released from the tooth upon completion of the dental procedure.

From yet another aspect, the invention permits the matrix retainer clamp described above to adjust to whatever mouth quadrant may be required. As previous matrix clamps have replaceable bands, a band is installed in them just prior to use and in the proper orientation dependent upon mouth quadrant. A band would last for several fillings or until it became too deformed for proper service. When more than one filling was performed on a patient it was often necessary to remove and flip over the band in order to have the band taper in the correct direction. In addition, matrix bands were positioned with the band exiting substantially perpendicularly with respect to the clamp body, in either a left or a right direction. In accordance with this further aspect of the invention, the head element of the clamp is articulated, permitting it to be swiveled from side to side in a plane substantially perpendicular to the slot for receiving the flat end sections of the matrix band. The preinstalled matrix band may thus be swiveled to fit whatever mouth quadrant may be being worked upon at the time.

From still another aspect of the invention, the adjusting knob attached to the threaded shaft of the block has a first diameter on its portion nearest the shaft and a second diameter on its portion farthest from the shaft. The second diameter of the knob is smaller than the diameter of the tube in order to permit rapid rotation of the shaft and rapid retraction of a mounted matrix band from a tooth. The first diameter of the shaft is larger in order to permit careful tightening of a mounted matrix band about a tooth.

The invention may be better understood from the following more detailed description of a specific embodiment, taken in the light of the accompanying drawing and the appended claims.

The invention may be better understood from the following more detailed description of a specific embodiment, taken in the light of the accompanying drawings and the appended claims.

DETAILED DESCRIPTION

Figure 1:
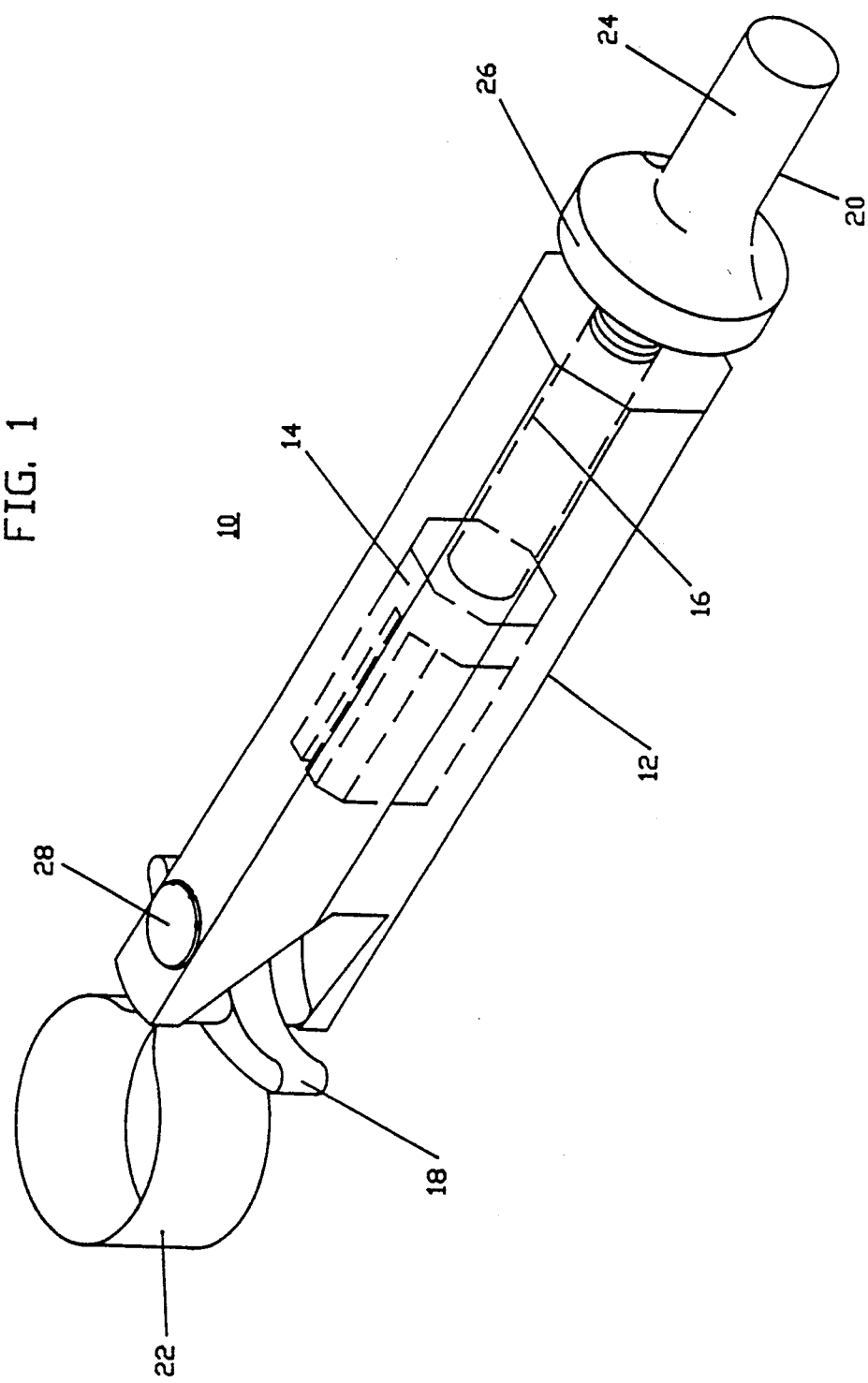
FIG. 1 is a perspective view of a loaded matrix retainer clamp embodying the various aspects of the invention.

In FIG. 1, an "Omni-Matrix System" 10 is made up of a hollow tube 12, a block 14 having a threaded shaft 16, a head element 18, a adjusting knob 20, and an installed metal matrix band 22. Tube 12, block 14, head element 18, and adjusting knob 20 constitute a disposable matrix retainer clamp, in which matrix band 22 is installed. The loop of matrix band 22 may be either cylindrical, as shown, or slightly conical.

Hollow tube 12 has threads extending longitudinally along the portion of its interior in which shaft 16 is installed, with the threads of shaft 16 mating with those of tube 12. Adjusting knob 20 is attached to the end of shaft 16 and, as shown, has a small diameter section 24 and a larger diameter section 26. The diameter of section 26 is, by way of example, substantially equal to the outside diameter of tube 12, while that of section 24 is only half as great or less. Head element 18, which is located at the opposite end of tube 12 from knob 20, is articulated in that it is held in place by a mounting pin 28 extending through the outside wall of tube 12 and can be swiveled from side to side. A similar mounting pin extends through the outside wall of tube 12 on the opposite side. The fit between head element 18 and mounting pin 28 is tight enough so that once head element has been given the desired orientation it tends to retain that orientation. Matrix band 22 has already been formed in a manner which will be described and extends through a slot (not shown in FIG. 1) in head element 18 into the interior of tube 12 in the direction of block 14.

All or any of the components of the retainer clamp in FIG. 1 may, in accordance with one aspect of the invention, be fabricated of plastic, thus further emphasizing disposability by reducing costs to a bare minimum. By way of example, tube 12, block 14 (along with its threaded shaft 16), head element 18, and adjusting knob 20 may, for example, all be of plastic material.

Figure 2:
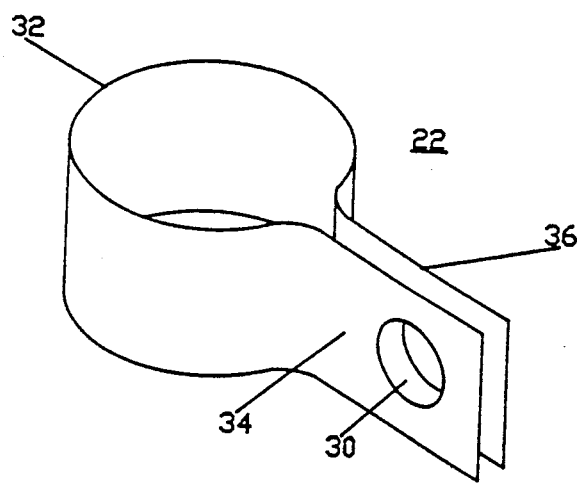
FIG. 2 is a perspective view of a fully formed matrix band ready for loading into a retainer clamp embodying the invention.

FIG. 2 gives a fuller perspective view of matrix band 22. Matrix band 22 has a hole 30 at each end and, when formed, has a central loop 32 and flat aligned end sections 34 and 36, each of which contains a hole 30. In the example shown in FIG. 2, loop 32 of band 22 is substantially cylindrical.

Figure 3:
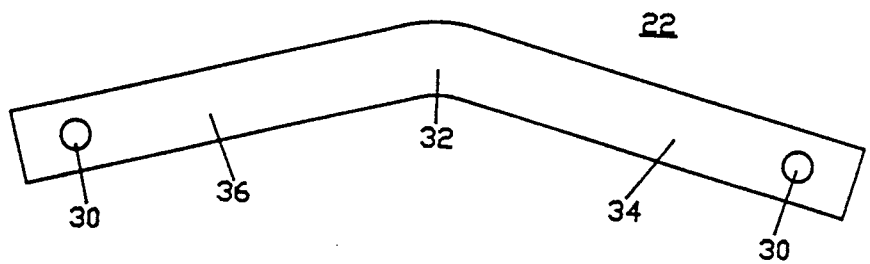
FIG. 3 is a plan view of one type of matrix band prior to forming.

FIG. 3 shows a plan view of an example of matrix band 22 as originally manufactured. In this example, band 22 is given the slight boomerang shape shown in FIG. 3 so that loop 32 will be slightly conical in shape when band 22 is formed. Alternatively, band 22 may have no boomerang like bend in the center at all and loop 32 will be cylindrical in shape as in the example shown in FIG. 2.

Figure 4:
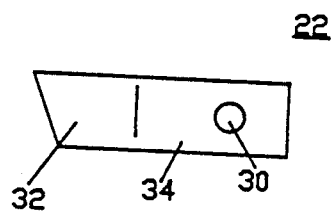
FIG. 4 is a side view of the matrix band in FIG. 3 after forming.

FIG. 4 shows a side view of the matrix band 22 example of FIG. 3 after forming. As shown, hole 30 in end section 34 is in alignment with the hole in the other end section (not shown). The slightly conical shape of loop 32 when formed from the matrix band 22 shown in FIG. 3 is illustrated.

Figure 5:
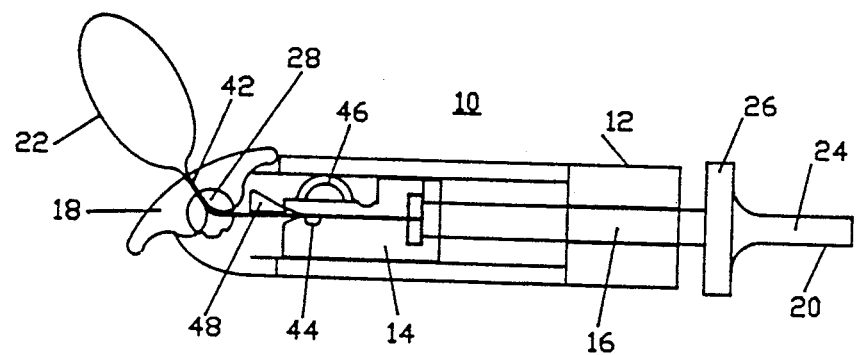
FIG. 5 is a cutaway view of a loaded matrix retainer clamp embodying the invention with the articulated head in a swiveled position and with the matrix band locked in place.

FIG. 5 is a cutaway view of loaded matrix retainer clamp 10 and shows some details of the invention not clearly visible in FIG. 1. Elements not previously described in detail include a slot 42 in head element 18 for receiving the end sections of matrix band 22, a spring mounted pin 44 for engaging the holes of the matrix band end sections, supporting structure 46 for pin 44 attaching it to block 14, and a wedge 48.

As shown in FIG. 5, head element 18 of retainer clamp 10 swivels about mounting pin 28 in the plane of the drawing and contains the slot 42 perpendicular to the plane of the drawing for receiving the end sections of matrix band 22. At the end of block 14 remote from shaft 16 and adjusting knob 20, the spring mounted pin 44 is held in place by the supporting structure 46 so that pin 44 extends through the holes in the end sections of matrix band 22. Matrix band 22 is thus held firmly in place and its loop can be tightened about a tooth whenever the dentist turns adjusting knob 20 (preferably by the large diameter fine adjustment section 26) in the direction to move block 14 to the right. The latter action pulls the rear portion of the loop of matrix band 22 into slot 42, making the remaining portion of the loop smaller and tighter about a tooth as block 14 moves to the right. As illustrated, head element 18 has small wings on either side to allow for added stability of the instrument against the sides of adjoining teeth.

The articulated nature and swiveling action of head element 18 are both emphasized in the view shown in FIG. 5. In FIG. 5, head element 18 is shown swiveled toward the top. It may, of course, remain straight or be swiveled by the same or any lesser amount in either direction. As shown, the face of head element 18 (the surface toward matrix band 22) is convex in shape. In this manner, the dentist is permitted to adjust the alignment of matrix band 22 to match the particular quadrant of the patient's mouth which is being worked on at the time.

Wedge 48 permits release of matrix band 22 in a manner which will be described later. Wedge 48 is mounted longitudinally within tube 12 between head element 18 and pin 44 and has its narrow end extending toward block 14. Since FIG. 5 is a cutaway view, only a single wedge 48 is shown and it is located just to the side (away from the viewer in the drawing) of the end sections of matrix band 22. Typically, another matching wedge 48 is located on the other side of the matrix band end sections (toward the viewer in the drawing).

Figure 6:
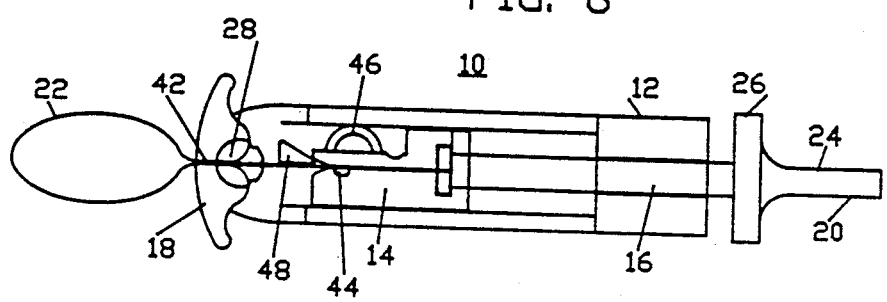
FIG. 6 is a cutaway view of a loaded matrix retainer clamp embodying the invention with the articulated head in a straight position and with the matrix band locked in place.

FIG. 6 is substantially identical to FIG. 5 except for the alignment of head element 18 and, hence, the loop of matrix band 22. In FIG. 6, head element 18 is shown in its straight position.

Figure 7:
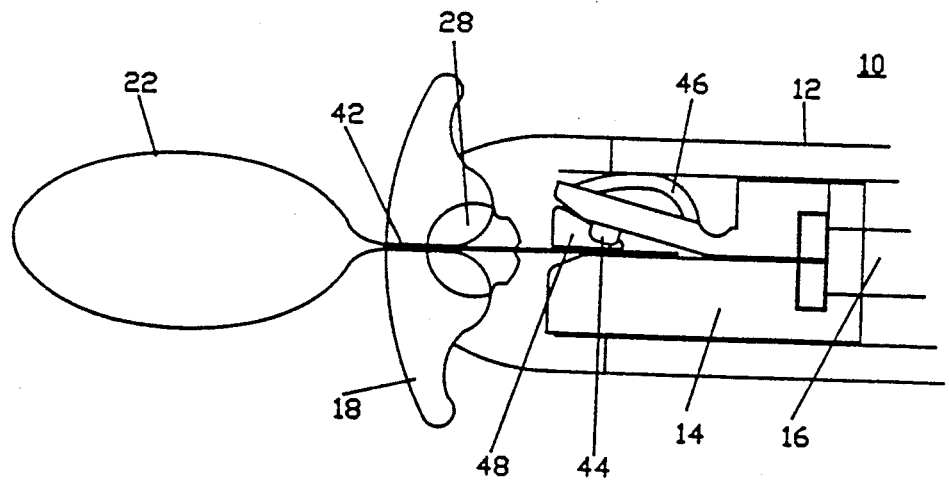
FIG. 7 is an enlargement showing details of the loaded matrix retainer illustrated in FIGS. 5 and 6 with the matrix band released.

FIG. 7 shows how the loaded matrix retainer clamp 10 operates to release matrix band 22 when threaded shaft 16 is rotated in the direction to move block 14 to the left, closer to head element 18. As illustrated, the supporting structure 46 for spring loaded pin 44 encounters wedge 48. This action forces pin 44 out of the holes in the end sections of matrix band 48. Typically, the dentist uses the small diameter section 24 of adjusting knob 20 (shown in FIGS. 1, 5, and 6) for this action. Once pin 44 has been forced out of the matrix band holes, matrix band 22 is released and cannot be reinstalled. The dentist is thus forced to discard the entire clamp and matrix band as an entity.

In summary, the "Omni-Matrix" tool 10 shown in FIGS. 1, 5, 6 and 7 is preassembled and an articulating head element 18 is incorporated in order to provide simplicity of choice during use. Through its unique design, the dentist need only swivel head element 18 to the appropriate side for placing the matrix band. Since the tightening mechanism is entirely enclosed within the barrel of the instrument formed by tube 12, chances of lip or cheek entrapment are eliminated. As an added aspect, adjusting knob 20 has two separate diameters in order to allow for multi speed tightening or loosening of matrix band 22. Removal of matrix band 22 from a tooth can be done in reverse to the placement procedure without fear of twisting, as matrix band 22 is held firmly in a vertical fashion by the barrel formed by tube 12. Should it be desirable to free matrix band 22 from the clamp completely, a unique release feature has been incorporated which renders the specific unit non-reusable and eliminates chances of patient cross contamination.

It is to be understood that the embodiment of the invention which has been described is illustrative. Numerous other arrangements and modifications may be readily devised by those skilled in the art without departing from the spirit and scope of the invention.

What is claimed is:

1. A dental matrix retainer clamp for holding a matrix band, said matrix band having a hole at each end and comprising, when formed, a central loop and flat aligned end sections each containing one of said holes, said matrix retainer clamp comprising:
   a hollow tube with threads extending longitudinally along at least a portion of its interior;
   a block extending longitudinally inside said tube and having a threaded shaft at one end mating with the threads of said tube;
   a head element at the end of said tube containing the end of said block opposite said shaft, said head element containing a slot for receiving the flat end sections of a matrix band with its holes extending beyond said head element into the interior of said tube;
   a pin spring mounted on the end of said block nearest said head element for engaging the holes of a matrix band having its end sections extending through said head element slot;
   at least one wedge mounted longitudinally within said tube with its narrow end extending in the direction toward said block to engage said pin spring and lift said pin clear of the holes of a matrix band having its end sections extending through said head element slot when said matrix band is moved into its extreme extended position with respect to said head element; and
   an adjusting knob attached to the threaded shaft of said block at the end of said tube opposite to said head element;
   said block moving in one direction under the control of said knob to tighten the loop of a matrix band mounted with its end sections extending through said head element slot and in the opposite direction to loosen said loop and cause said wedge to release said pin from the matrix band holes.

2. A dental matrix retainer clamp in accordance with claim 1 in which said hollow tube, said block, said head element, said pin, said wedges, and said adjusting knob are all of plastic material.

3. A dental matrix retainer clamp in accordance with claim 2 in combination with:
 a matrix band having a hole at each end and comprising, when formed, a central loop and flat aligned end sections each containing one of said holes;
 said matrix band being loaded into said clamp with its end sections extending through said head element slot so that said pin engages said holes.

4. A dental matrix retainer clamp in accordance with claim 1 in which:
 two wedges are mounted longitudinally within said tube on opposite sides of said pin with their narrow ends extending in the direction toward said block to engage the mounting of said pin and selectively lift said pin clear of the holes of a matrix band having its end sections extending through said head element slot when said matrix band is moved into its extreme extended position with respect to said head element.

5. A dental matrix retainer clamp in accordance with claim 4 in which said hollow tube, said block, said head element, said pin, said wedges, and said adjusting knob are all of plastic material.

6. A dental matrix retainer clamp in accordance with claim 5 in combination with:
 a matrix band having a hole at each end and comprising, when formed, a central loop and flat aligned end sections each containing one of said holes;
 said matrix band being loaded into said clamp with its end sections extending through said head element slot so that said pin engages said holes.

7. A dental matrix retainer clamp in accordance with claim 4 in which:
 said head element is articulated, permitting it to be swiveled from side to side in a plane substantially perpendicular to the slot for receiving the flat end sections of a matrix band.

8. A dental matrix retainer clamp in accordance with claim 7 in combination with:
 a matrix band having a hole at each end and comprising, when formed, a central loop and flat aligned end sections each containing one of said holes;
 said matrix band being loaded into said clamp with its end sections extending through said head element slot so that said pin engages said holes.

9. A dental matrix retainer clamp in accordance with claim 7 in which:
 the surface of said head element is convex in a plane substantially perpendicular to said slot on the periphery of said head element facing the loop of a mounted matrix band.

10. A dental matrix retainer clamp in accordance with claim 9 in which said hollow tube, said block, said head element, said pin, said wedges, and said adjusting knob are all of plastic material.

11. A dental matrix retainer clamp in accordance with claim 10 in combination with:
 a matrix band having a hole at each end and comprising, when formed, a central loop and flat aligned end sections each containing one of said holes;
 said matrix band being loaded into said clamp with its end sections extending through said head element slot so that said pin engages said holes.

12. A dental matrix retainer clamp in accordance with claim 9 in which:
 said adjusting knob has a first diameter nearest said threaded shaft and a second diameter farther from said threaded shaft;
 said second diameter being smaller than the diameter of said tube to permit rapid rotation of said shaft and rapid retraction of a mounted matrix band from a tooth.

13. A dental matrix retainer clamp in accordance with claim 12 in which said hollow tube, said block, said head element, said pin, said wedges, and said adjusting knob are all of plastic material.

14. A dental matrix retainer clamp in accordance with claim 12 in combination with:
 a matrix band having a hole at each end and comprising, when formed, a central loop and flat aligned end sections each containing one of said holes;
 said matrix band being loaded into said clamp with its end sections extending through said head element slot so that said pin engages said holes.

15. A dental matrix retainer clamp in accordance with claim 12 in which:
 the first diameter of said adjusting knob is larger than said second diameter to permit careful tightening of a the loop of a mounted matrix band about a tooth.

16. A dental matrix retainer clamp in accordance with claim 15 in which said hollow tube, said block, said head element, said pin, said wedges, and said adjusting knob are all of plastic material.

17. A dental matrix retainer clamp in accordance with claim 16 in combination with:
 a matrix band having a hole at each end and comprising, when formed, a central loop and flat aligned end sections each containing one of said holes;
 said matrix band being loaded into said clamp with its end sections extending through said head element slot so that said pin engages said holes.

18. A dental matrix retainer clamp for holding a matrix band, said matrix band comprising, when formed, a central loop and flat aligned end sections, said matrix retainer clamp comprising:
 a hollow tube with threads extending longitudinally along at least a portion of its interior;
 a block extending longitudinally inside said tube and having a threaded shaft at one end mating with the threads of said tube;
 an articulating head element at the end of said tube containing the end of said block opposite said shaft, said head element containing a slot for receiving the flat end sections of a matrix band with portions of said end sections extending beyond said head element into the interior of said tube and said head element being capable of swiveling from side to side in a plane substantially perpendicular to said slot;
 means on said block for engaging the end sections of a matrix band extending through said head element slot; and
 an adjusting knob attached to the threaded shaft of said block at the end of said tube opposite to said head element;
 said block moving in one direction under the control of said knob to tighten the loop of a matrix band mounted with its end sections extending through said head element slot and in the opposite direction to loosen said loop.

19. A dental matrix retainer clamp in accordance with claim 18 in which the surface of said articulating head element is convex in a plane substantially perpendicular to said slot on the periphery of said head element facing the loop of a mounted matrix band.

20. A dental matrix retainer clamp in accordance with claim 19 in which said hollow tube, said block, said head element, said pin, and said adjusting knob are all of plastic material.

21. A dental matrix retainer clamp in accordance with claim 20 in combination with:

a matrix band comprising, when formed, a central loop and flat aligned end sections;

said matrix band being loaded into said clamp with its end sections extending through said head element slot so that said block is engaged therewith.

* * * * *